United States Patent [19]
Morris

[11] Patent Number: 5,967,484
[45] Date of Patent: *Oct. 19, 1999

[54] INTRAVENOUS TUBE OCCLUDER

[75] Inventor: Matthew G. Morris, San Diego, Calif.

[73] Assignee: Alaris Medical Systems, Inc., San Diego, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/576,188

[22] Filed: Dec. 21, 1995

[51] Int. Cl.$^6$ ..................................................... F16K 7/04
[52] U.S. Cl. ...................................... 251/4; 251/7
[58] Field of Search ............................... 251/4, 7

[56] References Cited

U.S. PATENT DOCUMENTS

| | | | |
|---|---|---|---|
| 207,469 | 8/1878 | Wolf. | |
| 1,344,433 | 6/1920 | Blackburn. | |
| 2,889,848 | 6/1959 | Redmer | 137/315 |
| 3,189,038 | 6/1965 | Von Pechmann | 137/315 |
| 3,926,175 | 12/1975 | Allen et al. | 128/1 R |
| 4,247,076 | 1/1981 | Larkin | 251/7 |
| 4,439,179 | 3/1984 | Lueders et al. | 251/7 X |
| 4,460,358 | 7/1984 | Somerville et al. | 640/250 |
| 4,586,691 | 5/1986 | Kozlow | 251/7 |
| 4,610,664 | 9/1986 | Harle | 604/119 |
| 4,689,043 | 8/1987 | Bisha | 604/250 |
| 4,728,324 | 3/1988 | Steigerwald et al. | 251/7 X |
| 4,818,190 | 4/1989 | Pelmulder et al. | 417/360 |
| 4,857,048 | 8/1989 | Simons et al. | 604/50 |
| 4,925,152 | 5/1990 | Huber | 251/5 |
| 4,932,629 | 6/1990 | Rodomista et al. | 251/4 |
| 5,017,192 | 5/1991 | Dodge et al. | 604/250 |
| 5,190,527 | 3/1993 | Hamilton et al. | 604/153 |
| 5,238,218 | 8/1993 | Mackal | 251/10 |
| 5,423,769 | 6/1995 | Jonkman et al. | 604/250 |
| 5,453,098 | 9/1995 | Botts et al. | 251/7 X |

FOREIGN PATENT DOCUMENTS

| | | | |
|---|---|---|---|
| 0423978 | 10/1990 | European Pat. Off. | A61M 5/142 |
| 0510881 A2 | 4/1992 | European Pat. Off. | A61M 39/00 |
| WO 93/05829 | 9/1992 | WIPO | A61M 5/00 |

Primary Examiner—John Fox
Attorney, Agent, or Firm—Pennie & Edmonds LLP

[57] ABSTRACT

A flexible tube occluder has a body portion and a slider portion which act to occlude a tube to prevent unwanted flow of fluid to a patient. The body portion and slider portion are engaged such that slider portion can move relative to body portion. The body portion extends the full range of slider portion's motion and thus the occluder allows for stable occluding and open positions. The slider portion has a slot of varying size which is used to occlude the tube by pressing the tube within the surface of the slot and to allow free flow of fluid through the tube.

19 Claims, 4 Drawing Sheets

INTRAVENOUS TUBE OCCLUDER

BACKGROUND OF THE INVENTION

The present invention generally relates to occluders for flexible tubing that prevent fluid flow through a portion of tubing. The present invention specifically relates to the selective occluding of an intravenous (IV) tube used to infuse liquid medication to a patient.

Intravenous infusion of medical solutions to patients is well known in the medical profession. Such infusion devices typically use a pump, such as a peristaltic pump, to create a moving zone of occlusion along a portion of an IV tube to administer fluid to a patient. The danger inherent in the use of the IV tube with a pump is that unwanted fluid will flow to the patient. Typically, the times of greatest concern for this danger are during the initial set-up of the IV administration system and at any subsequent time when the IV tube is connected between the fluid source and the patient and the IV tube becomes disengaged from the infusion device for some reason.

Various devices to constrict or occlude flow of liquid through tubes are described in the prior art. Typical devices include manually operated slide clamps. Roller clamps, such as the one described in U.S. Pat. No. 3,189,038, are one such example. A slide clamp of typical design is also described in U.S. Pat. No. 2,889,848. Both of these clamps are multi-element assemblies and both must be activated independently and separately from any medical device which may be operatively attached to the IV fluid line.

The need to coordinate the operation of a clamp or occluder with an associated medical device, such as a peristaltic pump has been recognized in the prior art as well. U.S. Pat. No. 4,586,691 discloses a safety slide clamp that requires the cooperation of structure between the device and the slide clamp itself. Another prior art slide clamp for an IV tube associated with an IV infusion pump is disclosed in U.S. Pat. No. 4,689,043. This device includes a peristaltic pump enclosed in a housing with a door and a door mounted handle for operatively engaging and disengaging the slide clamp. The disclosed clamp, however, includes several elements, each of which may require precision machine tolerances. U.S. Pat. No. 5,453,098 (U.S. Ser. No. 08/241, 041, filed May 9, 1994) discloses a fluid flow stop which protects against unintended actuation with a locking mechanism. The locking mechanism, however, somewhat complicates the user interface by requiring a two-step process. At a minimum, two hands are needed to manually manipulate the locking mechanism.

A product available from Medex Inc., known as the Trilogy™ Multichannel Infusion Pump, includes an optional flow clip on the disposable IV administration sets for use with the infusion pump. The flow clamp is a single piece of deformable plastic with two extending members that must be spread apart by the pump to open the tube, similar to a clothespin arrangement. In the relaxed state, the flow clamp occludes all flow of liquid through the tube. This structure is difficult to adapt for manual use, due to the fact that it is more difficult to spread two members apart, rather than pushing them together. In addition, the default to occluding the tube may lead to the permanent deformation of both the clamp and the tube itself.

SUMMARY OF THE INVENTION

In light of the above-described needs, it is an object of the present invention to provide an occluder for use with flexible tubing that is relatively cost-effective and may be used manually and/or in conjunction with common infusion pump devices.

It is a further object of the present invention to provide an occluder that can automatically and positively occlude a flexible tube before the infusion pumping mechanism is disengaged from the tube.

It is a further object of the present invention to provide an occluder that can automatically and positively maintain flexible tubing in an occluded state until after the infusion pumping mechanism is engaged with the tube.

It is a further object of the invention to provide an occluder that can reliably occlude and is stable in both open and occluding states.

These and other objects are met according to the present invention by a tube occluder which includes a body member and a slider member with the body member extending over the slider member's full range of sliding motion. Thus, because access to the slider member is controlled, only deliberate actuation of the tube occluder will move the slider member. The body member and slider member are engaged to define a passageway through the body member and the slider member and through which the tube to be occluded will be located.

The defined passageway includes a portion of a slot defined by the slider member. The slot has varying width and extends at least a portion of the length of the slider member. When the slider is in the occluding position, the interior surface of the slot applies pressure to the tube to occlude the tube. As the slider member is moved into the open or occluding position, the tube slides into an appropriately sized portion of the slot to open or occlude the tube. Once the slider member is in either the open or the occluding position, it is stable and will keep the tube open or occluded until an additional force is applied to the slider member in order to occlude or open the tube.

The defined passageway of the tube occluder may also include fitments extending from the body member. The fitments guide the tube from the body member to the slider member and prevent the tube from slipping away from the occluder. A piece of tubing to be occluded may be inserted into the defined passageway by threading the tubing through the fitments thereby directing the section of the tube to be occluded through a portion of the slot defined by the slider member.

Approximately one half of the body member of the tube occluder may be opaque or frosted and the remainder of the body member may be clear so that the slider member is visible when the slider member is in one state, preferably the occluding state, and not visible when the slider member is in the other state, preferably the open state. Thus, the state of the tube occluder can be identified by the user from a distance.

The tube occluder may be used in conjunction with an associated medical device, such as a peristaltic pump. The medical device may have a spring driven plunger to bias the slider member in the occluding position when the door of the medical device is open. The forces of the spring driven plunger may be overridden by an actuating feature such as on the back of a latch handle or other moving mechanism of the medical device so as to push the slider member from its occluding position to its open position as the door is closed. Specifically, the actuating feature is positioned to contact the slider member as the door closes and to work against the force of the spring driven plunger, thereby pushing the slider member to its open position. The body member of the occluder may also define a slot to accommodate the actuating feature of the medical device.

The tube occluder may also be actuated manually. The body member may have a thumb or finger pad on one side so as to increase the ease of manually actuating the slider member without compromising prevention of unintentional actuation of the tube occluder. The pad also makes the loading of the tube occluder into the associated medical device more intuitive and user friendly. In addition, the slider member may have a grip to assist in manual operation of the occluder.

The present invention provides advantages over known locking mechanism devices because it cannot be defeated by force. The displacement controlled occlusion of the present invention allows the slider to occlude flow on any tubing material with a substantially constant inner diameter and wall thickness. In contrast, force controlled locking mechanisms may not work with stiffer materials.

DETAILED DESCRIPTION

Figure 1:
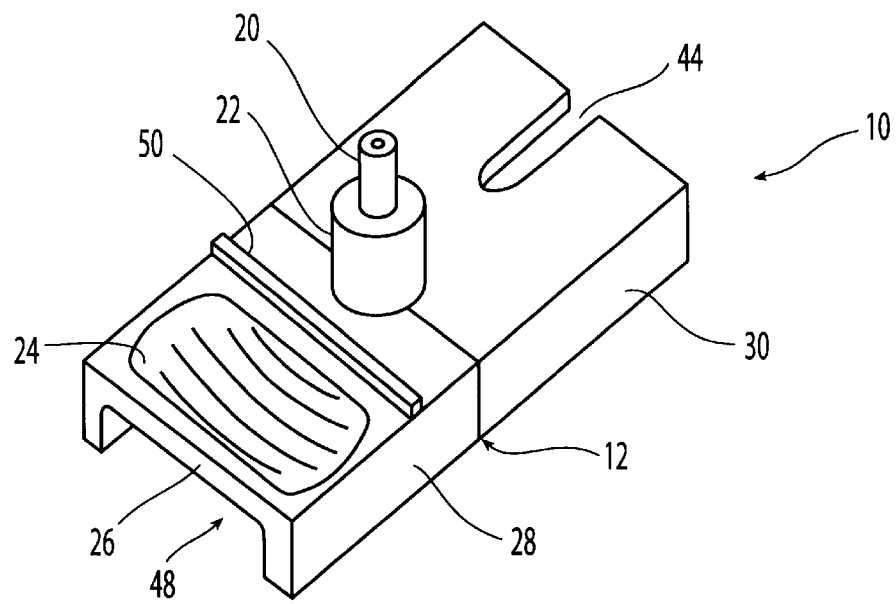
FIG. 1 is a top perspective view of one embodiment of the occluder of the present invention with the slider hidden behind the body.
Figure 2:
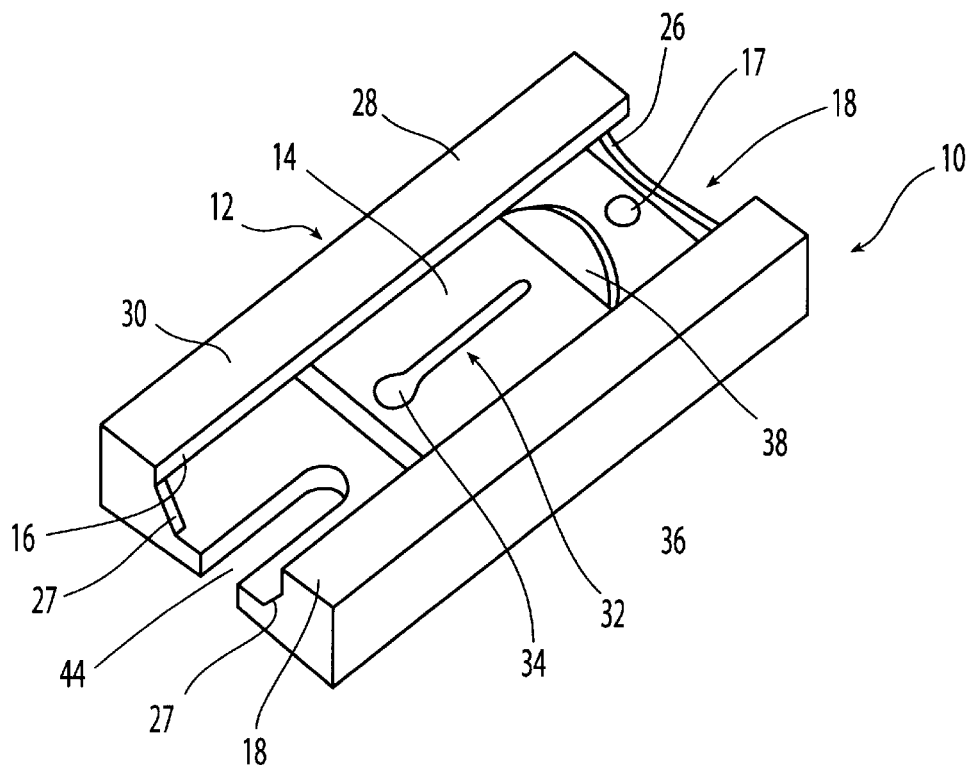
FIG. 2 is a bottom perspective view of the occluder of the present invention.

A preferred embodiment of occluder 10 of the present invention is shown in FIGS. 1 and 2. Occluder 10 has a body member 12 and a slider member 14. Body member 12 defines guides 16 and 18 which provide for engagement of body member 12 with slider member 14. Guides 16 and 18 permit slider member 14 to slide relative to body member 12, wherein body member 12 extends over slider member's full range of motion relative to body member 12. Slider 14 is therefore fully encompassed by body 12, regardless of the slider's position and does not extend beyond the periphery of the body member.

Figure 4:
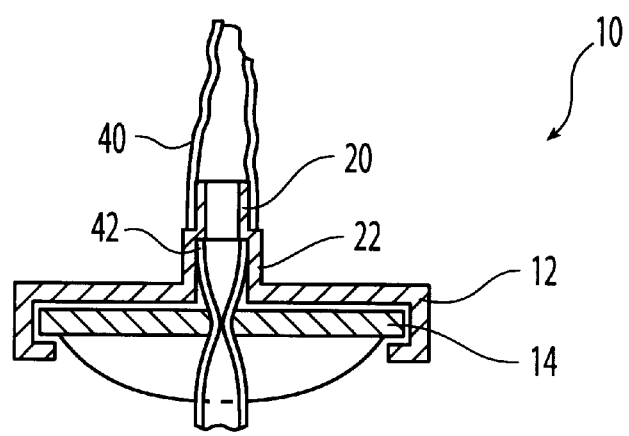
FIG. 4 is a cross-sectional view of the occluder of the present invention along line 4—4 in FIG. 3.
Figure 6:
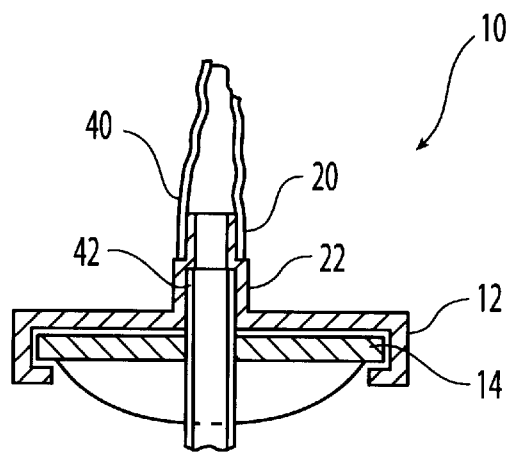
FIG. 6 is a cross-sectional view of the occluder of the present invention along line 6—6 in FIG. 5.

Occluder 10 preferably provides external fitment 20 and internal fitment 22, wherein internal fitment 22 extends from body member 12 and external fitment 20 further extends from internal fitment 22. Fitments 20 and 22 locate and bond segments of tube 40 to occluder 10 (as shown in FIGS. 4 and 6). Internal fitment 22 further guides tube 40 through slider member 14. Preferably, inner diameter of internal fitment 22 is slightly larger than outer diameter of tube 40 to allow for slight shifting of tube 40 with the sliding movement of slider member 14 relative to body member 12.

To prevent the slider member's range of sliding motion along guides 16 and 18 from continuing beyond body member 12, body member 12 defines first stops 26 to arrest the sliding motion of slider member 14 in one direction, and second stops 27 to arrest the sliding motion of slider member 14 in the other direction. Also, bump 17 on body 12 and ridge 19 on slider 14 cooperate in the open position to provide tactile response, such as a snap, when the occluder is fully open.

Body member 12 further may define thumb or finger pad 24 above first stop 26, which in conjunction with first stop 26, increases ease of manual actuation of slider member 14 and makes loading of occluder 10 into a device more intuitive and user friendly. Grip 38 of slider member 14 additionally increases ease of manual actuation of slider member 14 and can assist in loading and removing the occluder in and out of the associated medical device. At the same time, first stop 26 increases the difficulty of unintentional or accidental actuation of slider member 14 by partially shielding grip 38.

Figure 3:
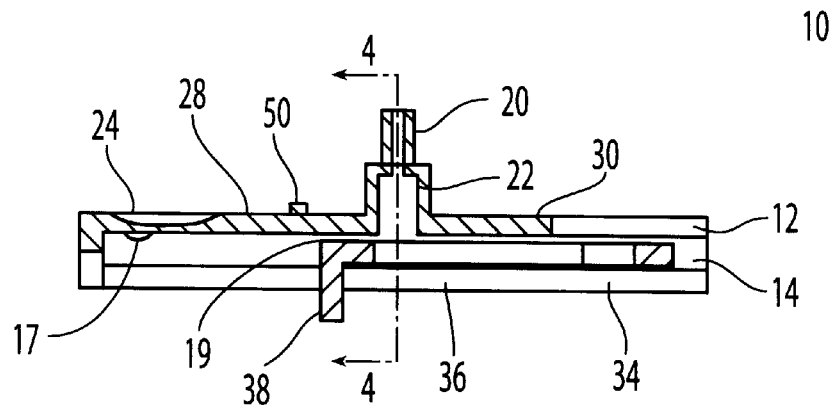
FIG. 3 is a side cross-sectional view of the occluder of the present invention in the occluding position.
Figure 5:
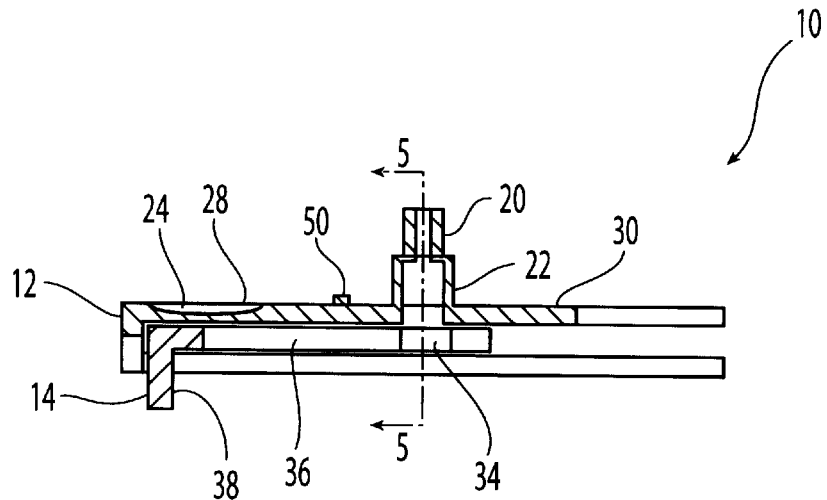
FIG. 5 is a side cross-sectional view of the occluder of the present invention in the open position.

Preferably, first end 28 of body member 12 is made of an opaque material and second end 30 of body member 12 is made of a clear material. Thus, when slider member 14 is in the occluding position (as shown in FIGS. 3 and 4), slider member 14 is situated at clear end 30 of body member 12 such that slider member 14 can be visible from a distance. Similarly, when slider member 14 is in the open position (as shown in FIGS. 5 and 6), slider member 14 is situated at opaque end 28 of body member 12 such that slider member 14 is not visible from a distance. With this configuration, a user can positively determine that occluder 10 is in the occluding state from a distance when slider member 14 can be seen through the clear end.

As shown in FIG. 2, slider member 14 defines slot 32 through which tube 40 (shown in FIGS. 4 and 6) is located. Slot 32 has an enlarged portion 34 and a narrower occluding portion 36. When slider member 14 is in the occluding position (FIGS. 3 and 4), occluding portion 36 of slot 32 is located adjacent to internal fitment 22, thereby situating tube 40 through occluding portion 36. (The tube is omitted from FIGS. 3 and 5 for greater clarity.) Because the size of occluding portion 36 of slot 32 is a predetermined amount smaller than that of tube 40, the interior surface of occluding portion 36 of slot 32 compresses and occludes tube 40, thereby preventing flow through tube 40. Similarly, when slider member 14 is in the open position (FIGS. 5 and 6), enlarged portion 34 of slot 32 is located adjacent to internal fitment 22, thereby situating tube 40 through enlarged portion 34. Because the size of enlarged portion 34 of slot 32 is approximately the same or larger than that of tube 40, tube 40 is not compressed and thus fluid can flow through tube 40.

Referring now to FIGS. 3–6, the operation of occluder 10 will be described in greater detail. FIGS. 3 and 4 show occluder 10 in the occluding position, wherein slider member 14 is at the clear end 30 of body member 12, as previously described. When slider member 14 is in the occluding position, tube 40 is located through occluding portion 36 of slot 32 and is compressed by inner surface of occluding portion 36, thereby occluding passage of fluid through tube 40. FIGS. 5 and 6 show occluder 10 in the open position, wherein slider member 14 is preferably at the opaque second side 30 of body member 12, as previously described. When slider member 14 is in the open position, tube 40 is located through enlarged portion 34 of slot 32 and is not compressed. Thus, slot 32 is not occluding, but rather, is allowing passage of fluid through tube 40.

To occlude a portion of tube 40, slider member 14 is moved along guides 16 and 18, either manually or automatically in cooperation with structure of an infusion pump device, from first end 28 to second end 30 of body member 12. This movement of slider member 14 causes tube 40 to shift from enlarged portion 34 to occluding portion 36 of slot 32. Thus, as tube 40 is situated in occluding portion 36, inner surface of occluding portion 36 compresses tube 40, as previously described. In addition, fitments 20 and 22 prevent tube 40 from slipping away from body member 12 despite the shifting of tube 40 along slot 32 of slider member 14.

The design of occluder 10 allows for two stable positions, occluding (shown in FIGS. 3 and 4), and open (shown in FIGS. 5 and 6). Because body member 12 extends the full range of motion of slider member 14, body member 12 protects slider member 14 from unintended actuation when slider member 14 is in either the open or occluding position.

Figure 7:
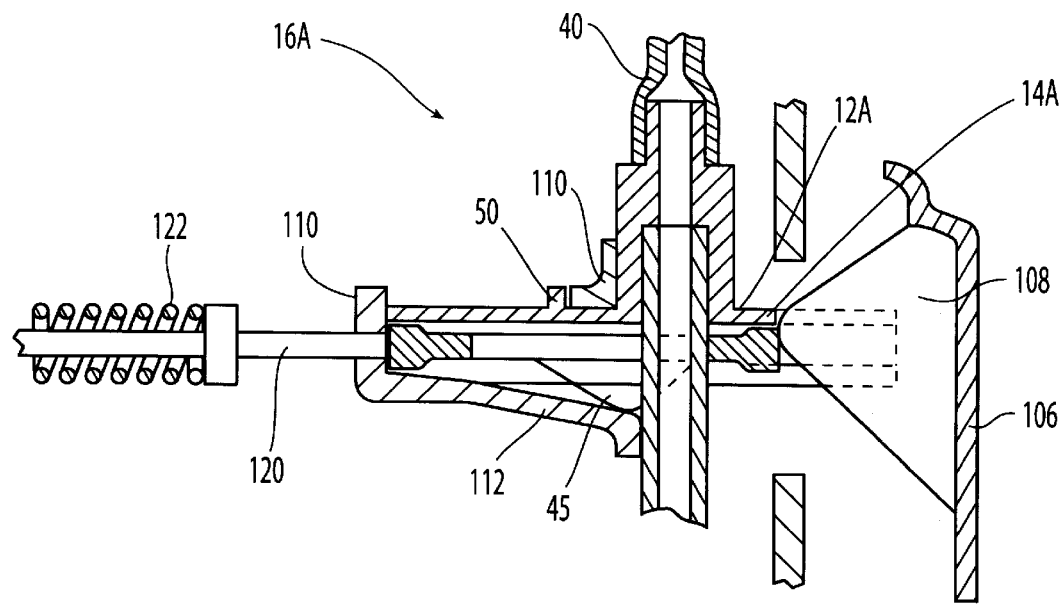
FIG. 7 is a cross-sectional view of an alternative embodiment of the occluder of the present invention in the open position, interacting with an associated medical device.
Figure 8:
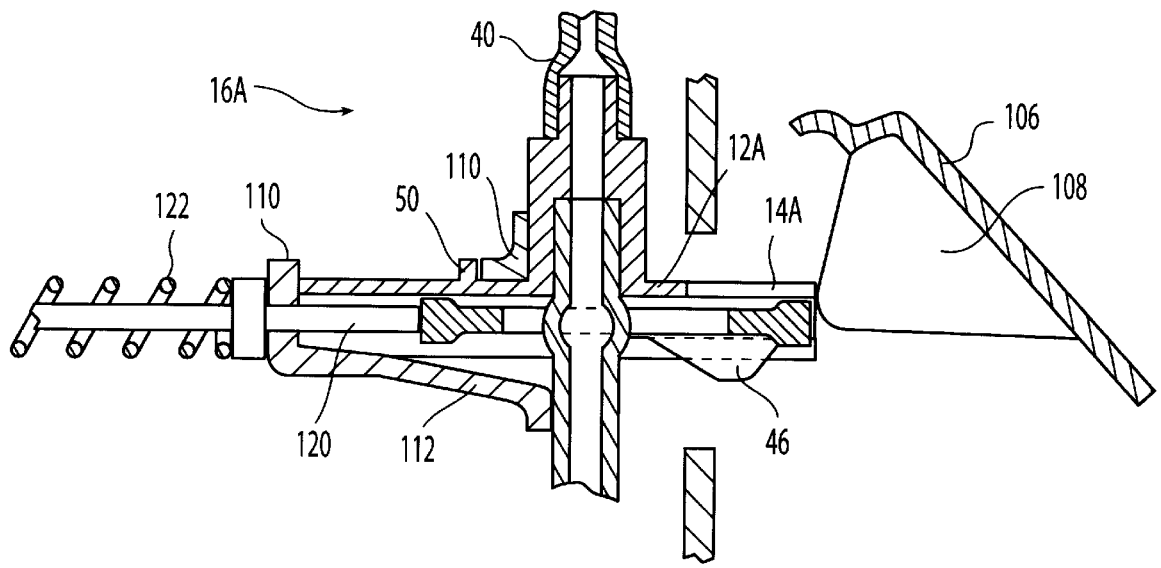
FIG. 8 is a cross-sectional view of the occluder in FIG. 7 in the occluding position, interacting with an associated medical device.

FIGS. 7 and 8 show occluder 10A, an alternative embodiment of the present invention, interfacing with an associated medical device. FIG. 7 shows occluder 10A in the open position while FIG. 8 shows occluder 10A in the occluding position. When door of the medical device is open, plunger 120, driven by spring 122, contacts one end of slider member 14 and biases it to the occluding position. The door can be opened and closed via latch 106 which has actuating member 108 positioned to engage one end of slider member 14, opposite the end of the member against which spring driven plunger 120 is biased. Thus, as the door closes, actuating member 108 engages one end of slider member 14, overrides the force of spring 122, and moves slider member 14 from the occluding position to the open position. When the door is completely closed, actuating member 108 fully engages slider member 14 such that slider member 14 is in the open position allowing for free flow of fluid through tube 40. Furthermore, body member 12 may define slot 44 to accommodate actuating member 108 as the door closes such that actuating member 108 at least partially occupies slot 44 as it pushes on slider member 14 against the forces of the spring driven plunger.

Thus, while the door is open, such as during set up or dismantling of the associated medical device, occluder 10A prevents inadvertent free flow of fluid through tube 40. In addition, with the spring driven plunger, no mechanism on the door is necessary to pull slider member 14 from the open position into the occluding position, thereby eliminating the problems of accurately positioning any such pulling mechanism on the door.

To ease loading of occluder 10A into the associated medical device, housing 110 may define downwardly-sloping ramp 112. Slider member 14A of occluder 10A may define support member 46, which, in conjunction with ramp 112, supports occluder 10A in the vertical axis when slider member 14A is in the open position, i.e. when support member 46 is in contact with ramp 112, thereby preventing excessive downward vertical motion of occluder 10A.

Body member 12A may also define open area 48 (better shown in FIGS. 1 and 2 for a similar embodiment) to accommodate the spring driven plunger such that the plunger engages grip 38 of the slider member and exerts spring forces thereon. The body member may further define retaining member 50 such that a portion of housing 110 is situated between internal fitment 22 and retaining member 50 as shown in FIG. 7. Thus, while the door of the associated medical device is open, the body member is retained in housing 110 as the forcer of spring 122 urges retaining member 50 against portion of housing 100. The body member is shaped to cooperate with the housing to ensure that it is properly loaded and seated in the housing when the door is closed.

While the particular embodiments of the tube occluder described and shown herein are fully capable of obtaining the objects and providing the advantages stated above, it is to be understood that they are merely illustrative of the presently preferred embodiments of the invention and that no limitations are intended to the details of construction or design herein shown other than as described in the appended claims.

What is claimed is:

1. A device for occluding tubing, comprising:

a first member having a body portion defining a periphery and having at least one guide portion, said first member also defining a hole for receiving the tubing to be occluded, wherein said periphery surrounds without intersecting said tubing; and a second member slidably secured to the first member and being retained by said at least one guide portion, said second member slidable between an occluding position and a non-occluding position such that the second member cooperates with the first member to alternately occlude and non-occlude the tubing corresponse to the movement of the second member, wherein the second member in both the occluding position and the non-occluding position is retained within an area defined by the periphery of the first member body portion, thereby protecting the second member from unintended actuation.

2. The device of claim 1, wherein the second member defines an elongated slot having a tapered opening with wider and narrower ends for receiving a tube to be occluded therethrough, wherein said wider end is aligned with said first member hole in the non-occluding position and said narrower end is aligned with said first member hole in the occluding position.

3. The device of claim 1, wherein:

said first member body portion comprises a body member having two opposed ends and two opposed sides; and said at least one guide portion comprises a rail member extending downward from each said side of the body member and surrounding a part of the second member, thereby slidably retaining said second member.

4. The device of claim 3, wherein said first body portion includes at least one stop member positioned to prevent movement of the second member beyond the periphery of the first member.

5. The device of claim 1, wherein said first member body portion includes surface defining a plane in which said hole and said periphery lie, and wherein said second member includes an actuating member extending away from said plane.

6. The device of claim 5, wherein said actuating member extends substantially perpendicularly to the plane.

7. A device for selectively preventing fluid flow through a flexible tube having an outer diameter, comprising:

a first member having first and second end and defining a first member periphery and a first opening lying within said periphery for receiving the tube therein; and a second member defining a second opening for receiving the tube therein, said second member being movable relative to the first member thereby defining a range of motion, wherein said second member is contained within said first member periphery over said range of motion of the second member and the second member is movable relative to the tube such that said movement causes the second member to alternate between an open position wherein fluid can flow through the tube and an occluding position wherein the tube is occluded by the second member, wherein the first member further comprises at least one guide wherein the second member is movable along said at least one guide over the range of motion and said at least one guide secures the second member to the first member for sliding movement there between.

8. A device for selectively preventing fluid flow through a flexible tube having an outer diameter, comprising:

a first member having first and second end and defining a first member periphery and a first opening lying within said periphery for receiving the tube therein; and a second member defining a second opening for receiving the tube therein, said second member being movable relative to the first member thereby defining a range of motion, wherein said second member is contained within said first member periphery over said range of motion of the second member and the second member is movable relative to the tube such that said movement causes the second member to alternate between an open position wherein fluid can flow through the tube and an occluding position wherein the tube is occluded by the second member, wherein the first member comprises a first end portion made of a clear material and a second end portion made of an opaque material such that the second member is visible to an observer when in the first end portion.

9. A tube occluder, comprising:

a body member defining a body member periphery and including a fitment element lying within said body member periphery for securing a tube therein such that a periphery projection of said body member periphery onto a plane would surround a fitment projection of a portion of said fitment element which is connected to said body member onto said plane; and a slider member having an opening for receiving the tube therethrough movable relative to the body member thereby defining a range of motion for the slider member, said slider member movement causes said slider member to cooperate with the body member to selectively occlude the tube; and means for limiting the range of motion of said slider member such that a slider member projection of said slider member onto said plane is within said periphery projection.

10. The tube occluder of claim 9, wherein the fitment element comprises means for guiding the tube to the body member and the slider member.

11. The tube occluder of claim 10, wherein the means for guiding the tube comprises means for retaining the tube in the fitment element and the slider member opening.

12. The tube occluder of claim 9, wherein the slider member opening comprises a tapered slot.

13. The tube occluder of claim 12, wherein the slot comprises means for contacting and compressing the tube.

14. The tube occluder of claim 12, wherein the slot comprises means for allowing free flow through the tube.

15. The tube occluder of claim 9, wherein said slider member has a surface defining said opening, said tube occluder further comprising a grip extending away from said surface such that the slider member and the grip are retained within said body member periphery.

16. A device for occluding tubing, comprising:

a first member defining a hole for receiving tubing and having a first surface through which said hole extends and which has at least one edge which defines an enclosed perimeter;

a second member slidably connected to said first member and positioned within said perimeter of said first surface such that said first surface covers said second member, said second member defining a slot having a first end which slidably aligns with said hole and receives said tubing in a non-occluded form and a second end which is more narrow than said first end and which alternatively slidably aligns with said hole and occludes said tubing; and means for restricting the travel of said second member to within said perimeter of said first surface.

17. The device of claim 16 wherein said first surface is planar.

18. The device of claim 16 wherein said means for restricting includes at least two edges of said first member.

19. The device of claim 16 further comprising at least one guide portion connected to said first member and slidably connected to said second member, and wherein said means for restricting includes at least two stops positioned at opposite ends of said at least one guide portion.

* * * * *